(12) United States Patent
Hennessey et al.

(10) Patent No.: US 8,445,236 B2
(45) Date of Patent: *May 21, 2013

(54) BIOMASS PRETREATMENT

(75) Inventors: Susan Marie Hennessey, Avondale, PA (US); Julie Friend, Claymond, DE (US); Richard T. Elander, Evergreen, CO (US); Melvin P. Tucker, III, Lakewood, CO (US)

(73) Assignees: Alliance for Sustainable Energy LLC, Golden, CO (US); E I du Pont de Nemours and Company, Wilmington, DE (US)

( * ) Notice: Subject to any disclaimer, the term of this patent is extended or adjusted under 35 U.S.C. 154(b) by 587 days.

This patent is subject to a terminal disclaimer.

(21) Appl. No.: 11/843,157

(22) Filed: Aug. 22, 2007

(65) Prior Publication Data

US 2009/0053770 A1    Feb. 26, 2009

(51) Int. Cl.
*C12P 19/00* (2006.01)

(52) U.S. Cl.
USPC ............................. 435/72; 435/99; 435/163

(58) Field of Classification Search
USPC .............................................. 435/72, 99, 163
See application file for complete search history.

(56) References Cited

U.S. PATENT DOCUMENTS

| | | | |
|---|---|---|---|
| 4,136,207 A | 1/1979 | Bender | |
| 4,186,658 A | 2/1980 | Brown | |
| 4,461,648 A | 7/1984 | Foody | |
| 4,859,283 A | 8/1989 | Jayawant | |
| 5,008,473 A | 4/1991 | Breitkopf et al. | |
| 5,037,663 A | 8/1991 | Dale | |
| 5,192,673 A | 3/1993 | Jain et al. | |
| 5,356,812 A | 10/1994 | Matsuyama et al. | |
| 5,366,553 A | 11/1994 | Lair et al. | |
| 5,705,369 A | 1/1998 | Torget et al. | |
| 5,879,463 A | 3/1999 | Proenca | |
| 5,916,780 A | 6/1999 | Foody et al. | |
| 6,013,494 A | 1/2000 | Nakamura et al. | |
| 6,090,595 A | 7/2000 | Foody et al. | |
| 6,159,738 A | 12/2000 | Donnelly et al. | |
| 6,176,176 B1 | 1/2001 | Dale et al. | |
| 6,228,630 B1 | 5/2001 | Kofod et al. | |
| 6,254,914 B1 | 7/2001 | Signh et al. | |
| 6,358,716 B1 | 3/2002 | Bulthuis et al. | |
| 6,358,717 B1 | 3/2002 | Blaschek et al. | |
| 6,514,733 B1 | 2/2003 | Emptage et al. | |
| 6,777,207 B2 | 8/2004 | Kjeldsen et al. | |
| 6,861,237 B2 | 3/2005 | Anderson et al. | |
| 6,962,805 B2 | 11/2005 | Asakura et al. | |
| 2003/0162271 A1 | 8/2003 | Zhang et al. | |
| 2003/0170834 A1 | 9/2003 | Gatrnby et al. | |
| 2004/0016525 A1 | 1/2004 | Gervais | |
| 2004/0231060 A1 | 11/2004 | Burdette et al. | |
| 2005/0161038 A1 | 7/2005 | Pinatti et al. | |
| 2005/0250192 A1 | 11/2005 | Shanmugan et al. | |
| 2006/0003429 A1 | 1/2006 | Frost et al. | |
| 2007/0031918 A1 | 2/2007 | Dunson, Jr. et al. | |

FOREIGN PATENT DOCUMENTS

| | | |
|---|---|---|
| EP | 0 263 515 A2 | 4/1988 |
| EP | 0 332 234 B1 | 9/1989 |
| EP | 136359 B1 | 4/1991 |
| FR | 656385 A | 5/1929 |
| JP | 47004505 | 3/1972 |
| JP | 47038995 | 10/1972 |
| JP | 51006237 | 1/1976 |
| JP | 51019037 | 2/1976 |
| JP | 54032070 | 3/1979 |
| JP | 54037235 | 3/1979 |
| JP | 56008596 | 1/1981 |
| JP | 56008596 B | 2/1981 |
| JP | 56010035 | 2/1981 |
| JP | 57150381 | 9/1982 |
| JP | 3207079 | 9/1991 |
| JP | 3723579 | 9/2005 |
| JP | 3899572 | 1/2007 |
| WO | 94/03646 | 2/1994 |
| WO | 03/078644 | 9/2003 |
| WO | 2004/018645 | 3/2004 |
| WO | 2004/081185 | 9/2004 |
| WO | WO 2007/041269 A2 | 4/2007 |
| WO | WO 2007/050671 A2 | 5/2007 |

OTHER PUBLICATIONS

Kim et al. 2006. Pretreatment of Corn Stover by Low-Liquid Ammonia Recycle Percolation Process. Applied Biochemistry and Biotechnology. vol. 133: p. 41-57.*
U.S. Appl. No. 11/741,892, filed Apr. 30, 2007, Gail K. Donaldson et al.
U.S. Appl. No. 11/741,916, filed Apr. 30, 2007, Gail K. Donaldson et al.
U.S. Appl. No. 60/847,813, filed Sep. 28, 2006, Paul V. Vitanen et al.
U.S. Appl. No. 60/847,856, filed Sep. 28, 2006, Paul V. Vitanen et al.
U.S. Appl. No. 11/403,087, filed Apr. 12, 2006, James B. Dunson, Jr. et al.

(Continued)

*Primary Examiner* — Taeyoon Kim

(57) ABSTRACT

A method is provided for producing an improved pretreated biomass product for use in saccharification followed by fermentation to produce a target chemical that includes removal of saccharification and or fermentation inhibitors from the pretreated biomass product. Specifically, the pretreated biomass product derived from using the present method has fewer inhibitors of saccharification and/or fermentation without a loss in sugar content.

23 Claims, No Drawings

OTHER PUBLICATIONS

U.S. Appl. No. 11/402,464, filed Apr. 12, 2006, James B. Dunson, Jr. et al.

Lynd et al., Microbial Cellulose Utilization: Fundamentals and Biotechnology, Microbiol. Mol. Biol. Rev., 2002, vol. 66:506-577.

Lin et al., Chemical Engineer's Handbook, 5$^{th}$ Edition, 1973, Chapter 4, McGraw-Hill, NY (Book Not Included).

Eur J. Biochem., Nomeclature Committee of The International Union of Biochemistry and Molecular Biology, Supplement: Corrections and Additions, 1994, vol. 223:1-5.

Eur. J. Biochem., Nomenclature Committee of The International Union of Biochemistry and Molecular Biology, Supplement 2: Corrections and Additions, 1995, vol. 232:1-6.

Eur J. Biochem., Nomenclature Committee of The International Union of Biochemistry and Molecular Biology, Supplement 3: Corrections and Additions, 1996, vol. 237:1-5.

Eur. J. Biochem., Nomenclature Committee of The International Union of Biochemisty and Molecular Biology, Supplement 4: Corrections and Additions, vol. 250:1-6.

Eur J. Biochem., Nomenclature Committee of The International Union of Biochemistry and Molecular Biology, Enzyme Supplement 5, 1999, vol. 264:610-650.

Miller, Use of Dinitrosalicylic Acid Reagent for Determination of Reducing Sugar, Anal. Chem., 1959, vol. 31:426-428.

Jones et al., Acetone-Butanol Fermentation Revisited, Microbiol. Rev., 1986, vol. 50:484-524.

Underwood et al., Genetic Changes to Optimize Carbon Partitioning Between Ethanol and Biosynthesis in ethanologenic *Escherichia coli*, Appl. Environ. Microbiol., 2002, vol. 68:6263-6272.

Zhou et al., Production of Optically Pure D-Lactic Acid in Mineral Salts Medium by Metabolically Engineered *Escherichia coli* W3110, Appl. Environ. Microbiol., 2003, vol. 69:399-407.

Tay et al., Production of L(+)-Lactic Acid From Glucose and Starch by Immobilized Cells of *Rhizopus oryzae* in a Rotating Fibrous Bed Bioreactor, Biotechnol. Bioeng., 2002, vol. 80:1-12.

Niu et al., Benzene-Free Synthesis of Adipic Acid, Biotechnol., Biotechnol. Prog., 2002, vol. 18:201-211.

Cheryan et al., Production of Acetic Acid by *Clostridium thermoaceticum*, Adv. Appl. Microbiol., 1997, vol. 43:1-33.

Freer, Acetic Acid Production by Dekkera/Brettanomyces Yeasts, World J. Microbiol. Biotechnol., 2002, vol. 18:271-275.

Lin et al., Metabolic Engineering of Aerobic Succinate Production Systems in *Escherichia coli* to Improve Process Productivity and Achieve the Maximum Theoretical Succinate Yield, Metab. Eng., 2005, vol. 7:116-127.

Li et al., Appl. Efficient Pyruvate Production by a Multi-Vitamin Auxotroph of *Torulopsis glabrata*? Key Role and Optimization of Vitamin Levels, Appl. Microbiol. Biotechnol. 2001, vol. 55:680-685.

Yokota et al., Pyruvic Acid Production by an F-Atpase-Defective Mutant of *Escherichia coli* W1485LIP2, Biosci. Biotech. Biochem., 1994, vol. 58:2164-2167.

Suwannakham et al., Enhanced Propionic Acid Fermentation by *Propionibacterium acidpropionici* Mutant Obtained by Adaptation in a Fibrous-Bed Bioreactor, Biotechnol. Bioeng., 2005, vol. 91:325-337.

Wu et al., Extractive Fermentation for Butyric Acid Production From Glucose by *Clostridium tyrobutyricum*, Biotechnol. Bioeng., 2003, vol. 82:93-102.

Janssen, Propanol as an End Product of Threonine Fermentation, Arch. Microbiol., 2004, vol. 182:482-486.

Anantassiadis et al., Process Optimization of Continuous Gluconic Acid Fermentation by Isolated Yeast-Like Strains of *Aureobasidium pullulans*, Biotechnol. Bioeng., 2005, vol. 91:494-501.

Singh et al., Optimisation of Fermentation Conditions for Gluconic Acid Production by a Mutant of *Aspergilllus niger*, Indian J. Exp. Biol., 2001, vol. 39:1136-1143.

Elfari et al., A Gluconobacter Oxydans Mutant Converting Glucose Almost Quantitatively to 5-Keto-D-Gluconic Acid, Appl. Microbiol. Biotech., 2005, vol. 66:668-674.

Reddy et al., Enhanced Production of Itaconic Acid from Corn Starch and Market Refuse Fruits by Genetically Manipulated *Aspergillus terreus* SKR10, Bioresur. Technol., 2002, vol. 85:69-71.

Ui-Haq et al., Optimization of Nitrogen for Enhanced Citric Acid Productivity by a 2-Deoxy D-Glucose Resistant Culture of *Aspergillus Niger* NGD-280, Bioresour. Technol., 2005, vol. 96:645-648.

Mussatto et al., Xylitol Production from High Xylose Concentration: Evaluation of the Fermentation in Bioreactor Under Different Stirring Rates, J. Appl. Microbiol., 2003, vol. 95:331-337.

Gorenflo et al., Development of a Process for the Biotech;nological Large-Scale Production of 4-Hydroxyvalerate-Containing Polyesters and Characterization of Their Physical and Mechanical Properties, Biomacromolecules, 2001, vol. 2:45-57.

Ui et al., Production of L-2,3-Butanediol by a New Pathway Constructed in *Escherichia coli*, Lett. Appl. Microbiol., 2004, vol. 39:533-537.

Okamoto et al., Development of an Industrially Stable Process for L-Threonine Fermentation by an L-Methionine-Auxotrophic Mutant of *Escherichia coli*, J. Biosci. Bioeng., 2000, vol. 89:79-87.

Kumar et al., Effect of Cysteine on Methionine Production by a Regulatory Mutant of *Corynebacterium lilium*, Bioresour. Technol., 2005, vol. 96:287-294.

Durre, New Insights and Novel Developments in Clostridial Acetone/Butanol/Isopropanol Fermentation, Appl. Microbiol. Biotechnol., 1998, vol. 49:639-648.

Groot et al., Technologies for Butanol Recovery Intergrated with Fermentations, Process Biochem., 1992, vol. 27:61-75.

Yamadaya et al., Hydrocracking of Tetralin on Supported Nicke-Tungsten Catalysts, Bullentin of the Chemical Society of Japan, 1977, vol. 50:79-87.

A.C. Waiss et al., Improving Digestibility of Straws for Ruminant Feed by Aqueous Ammonia, Journal of Animal Science, 1972, vol. 35:109-112.

U.S. Appl. No. 11/402,757, filed Apr. 12, 2006, James B. Dunson et al.

Gould, Alkaline Peroxide Delignification of Agricultural Residues to Enhance Enzymatic Saccharification, Biotech. and Bioengr., 1984, vol. 26:46-52.

Teixeira et. al., Alkaline and Peracetic Acid Pretreatments of Biomass for Ethanol Production, Appl. Biochem. and Biotech., 1999, vol. 77-79:19-34.

Elshafei et. al., The Saccharification of Corn Stover by Cellulase From *Penicillium funiculosum*, Bioresource Tech., 1991, vol. 35:73-80.

Kim et. al., Pretreatment and Fractionation of Corn Stover by Ammonia Recycle Percolation Process, Bioresourse Technology, 2005, vol. 96:2007-2013.

K. N. Joblin et. al., Fermentation of Barley Straw by Anaerobic Rumen Bacteria and Fungi in Axenic Culture and in Co-Culture With Methanogens, Letters in Applied Microbiology, 1989, vol. 9:195-197.

Kurakake et. al., Pretreatment With Ammonia Water for Enzymatic Hydrolysis of Corn Husk, Bagasse, and Switchgrass, Appiled Biochemistry and Biotechnology, 2001, vol. 90:251-259.

Taylor et. al., Corn Milling Pretreatment With Anhydrous Ammonia, Applied Biochemistry and Biotechnology, 2003, vol. 104:141-148.

Cao et. al., Production of 2, 3 Butanediol From Pretreated Corn Cob by *Klebsiella oxytoco* in the Presence of Fungal Cellulase, Applied Biochemistry and Biotechnology, 1997, vol. 63-65:129-139.

Cao et. al., Ethanol Production From Corn Cob Pretreated by the Ammonia Steeping Process Using Genetically Engineered Yeast, Biotechnology Letters, 1996, vol. 18:1013-1018.

Iyer et. al., Ammonia Recycled Percolation Process for Pretreatment of Herbaceous Biomass, Applied Biochemistry and Biotechnology, 1996, vol. 57-58:121-132.

D. Ben-Ghedalia et. al., The Effect of Chemical Pretreatments and Subsequent Enzymatic Treatments on the Organic Matter Digestibility In Vitro of Wheat Straw, Nutrition Reports International, 1979, vol. 19:499-505.

Mosier et. al., Features of Promising Technologies for Treatment of Lignocellulosic Biomass, Bioresource Technology, 2005, vol. 96:673-686.

Lee et al., Cellulose Hydrolysis Under Extremely Low Sulfuric Acid and High Temperature Conditions, Appl. Biochem. Biotech., 2001, vol. 91:331-340.

Nakayama et al., Fermentative Production of L-Arginine, Arg. Biol. Chem., 1972, vol. 36:675-1684.

Gusakov et al., Enhancement of Enzymatic Cellulose Hydrolysis Using a Novel Type of Bioreactor With Intensive Stirring Induced by Electromagnetic Field, Appl. Biochem. Biotechnol., 1994, vol. 56:141-153.

Ryu et al., Bioconversion of Waste Cellulose by Using an Attrition Bioreactor, Biotechnol. Bioeng., 1983, vol. 25:53-65.

Curreli et al., Complete and Efficient Enzymic Hydrolysis of Pretreated Wheat Straw, Process Biochem., 2002, vol. 37:937-941.

Teymouri et al., Optimization of the Ammonia Fiber Expolsion (AFEX) Treatment Parameters for Enzymatic Hydrolysis of Corn Stover, Bioresource Tech., 2005, vol. 96:2014-2018.

Barron et al., Ethanol Production by *Kluyveromyces marxianus* IMB3 During Growth on Straw-Supplemented Whiskey Distillery Spent Wash At 45 Degrees C., Bioprocess Engineering, 1997, vol. 17:383-386.

Kim et al., Pretreatment of Corn Stover by Soakingin Aqueous Ammonia, Applied Biochemistry & Biotechnology, 2005, vol. 121-124:1119-1131.

H. Hagino, Control Mechanisms in Aromatic Amino Acid Biosynthesis and the Amino Acid Production, Arg. Chem. Soc., Japan, 1976, vol. 50:R79-R87.

Aden et al., Biofuels for Sustainable Transportation, National Renewable Energy Laboratory Report TP-510-32438, 2000.

Lloyd et al., Combined Sugar Yields for Dilute Sulfuric Acid Pretreatment of Corn Stover Followed by Enzymatic Hydrolysis of the Remaining Solids, Bioresource Technology, 2005, vol. 96:1967-1977.

Gusakov et al., Kinetics of the Enzymatic Hydrolysis of Cellulose: 1. Mathematical for a Batch Reactor Process, Enz. Microb. Technol., 1985, vol. 7:346-352.

Isci et al., Applied Biochemistry and Biotechnology (2008) 144:69-77.

Kim et al., Bioresource Technology, (2005) 96:2007-2013.

International Search Report in related PCT/US2008/073420 mailed Jul. 14, 2009.

* cited by examiner

BIOMASS PRETREATMENT

STATEMENT OF GOVERNMENT RIGHTS

This invention was made with United States Government support under Contract Nos. 04-03-CA-70224 and DE-FC36-03GO13146 awarded by the Department of Energy. The government has certain rights in this invention.

FIELD OF THE INVENTION

A method is provided for producing an improved pretreated biomass product for use in saccharification to produce a high sugar content hydrolysate. Specifically, the pretreated biomass product derived from using the present method has fewer inhibitors of saccharification and/or fermentation.

BACKGROUND

Cellulosic and lignocellulosic feedstocks and wastes, such as agricultural residues, wood, forestry wastes, sludge from paper manufacture, and municipal and industrial solid wastes, provide a potentially large renewable feedstock for the production of valuable products such as fuels and other chemicals. Cellulosic and lignocellulosic feedstocks and wastes, composed of carbohydrate polymers comprising cellulose, hemicellulose, glucans and lignin are generally treated by a variety of chemical, mechanical and enzymatic means to release primarily hexose and pentose sugars, which can then be fermented to useful products.

First, biomass feedstocks are treated to make the carbohydrate polymers of cellulosic and lignocellulosic materials more readily available to saccharification enzymes, which is typically called pretreatment. The pretreated biomass is then further hydrolyzed in the presence of saccharification enzymes to release oligosaccharides and/or monosaccharides in a hydrolyzate. Saccharification enzymes used to produce fermentable sugars from pretreated biomass typically include one or more glycosidases, such as cellulose-hydrolyzing glycosidases, hemicellulose-hydrolyzing glycosidases, and starch-hydrolyzing glycosidases, as well as peptidases, lipases, ligninases and/or feruloyl esterases. Saccharification enzymes and methods for biomass treatment are reviewed in Lynd, L. R., et al. (Microbiol. Mol. Biol. Rev. (2002) 66:506-577).

During pretreatment of biomass, different components of cellulose, hemicellulose and lignin may be released that can include sugars and/or by-products, including compounds such as acetic acid, formic acid, levulinic acid, furaldehydes and phenolic compounds. Some of the by-products are inhibitors in that they affect the activities of saccharification enzymes and/or the growth and metabolism of microorganisms used in subsequent fermentation. These inhibitors can reduce the efficiencies of the saccharification and/or fermentation processes. Some attempts have been made to remove said inhibitors with additional steps, such as collection of sugars thereby creating a prehydrolyzate. These measures are unsatisfactory because they are not economical and result in reduced production of sugars.

Thus, there is a need for a pretreatment method that produces pretreated biomass having maximal retention of sugars and minimal presence of inhibitors, without forming a separate pretreatment sugar stream (prehydrolysate). This would provide a more economical and effective in-put biomass for use in saccharification followed by fermentation to produce useful products.

SUMMARY OF THE INVENTION

The present invention provides a method for preparing an improved pretreated biomass product comprising:
a) providing biomass;
b) pretreating said biomass by contacting said biomass under suitable conditions with an aqueous solution comprising ammonia to form a biomass-aqueous ammonia mixture, wherein the ammonia is present at a concentration at least sufficient to maintain alkaline pH of the biomass-aqueous ammonia mixture but wherein said ammonia is present at less than about 12 weight percent relative to dry weight of biomass, and further wherein the dry weight of biomass is at a high solids concentration of at least about 15 weight percent relative to the weight of the biomass-aqueous ammonia mixture whereby a pretreated biomass solids product and a biomass pretreatment liquor comprising one or more inhibitor compound is formed; and
c) removing said biomass pretreatment liquor;
wherein the pretreated biomass solids product has a reduced amount of inhibitor compounds and insubstantial reduction in sugar content.

In other aspects the method further comprises adding an additional aqueous component in one or more of the following ways:
i) prior to step (b)
ii) as an additional component in step (b); or
iii) after step (b) as a wash step.

Further, the pretreated biomass solids product may be saccharified to form a sugars hydrolysate which may then be fermented to produce a target chemical.

Additional aspects of the present invention are biomass that has been pretreated according to the present method, and hydrolysate produced by saccharification of biomass that has been pretreated by the present method. Yet other aspects are target chemicals produced by biocatalytic fermentation of hydrolysate produced by saccharification of biomass that has been pretreated by the present method.

Biomass refers to any cellulosic or lignocellulosic material, for example, bioenergy crops, agricultural residues, municipal solid waste, industrial solid waste, yard waste, wood, forestry waste and combinations thereof. The aqueous solution comprising ammonia may be derived from ammonia gas, ammonium hydroxide, urea, and combinations thereof. The aqueous solution comprising ammonia may comprise at least one additional base. In addition, in the present method, vacuum may be applied to the biomass prior to contacting the biomass with an aqueous solution comprising ammonia. Ammonia may also be removed prior to step (c); ammonia may be recycled back to the pretreatment reactor. The ammonia and biomass may be reacted in the present method at a temperature that is between about 4° C. and about 200° C. A plasticizer, softening agent or combination thereof may be used in the present method. In addition, energy may be applied to the biomass before, during, or after step (a) in order to reduce the size, increase the exposed surface area, and/or increase the accessibility to aqueous ammonia or saccharification enzymes.

DETAILED DESCRIPTION OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The present invention provides a method for pretreatment of biomass that reduces the amount of inhibitors in a pretreated biomass product. Due to the reduced presence of inhibitors, saccharification and fermentation processes for producing valuable products from said biomass are more efficient. Efficient use of renewable biomass, including waste biomass, to produce valuable chemicals may decrease the need for oil.

Definitions

In this disclosure, a number of terms are used. The following definitions are provided:

The term "fermentable sugar" or "sugars" refers to oligosaccharides and monosaccharides that can be used as carbon sources by a microorganism in a fermentation process.

The term "lignocellulosic" refers to a composition comprising both lignin and cellulose. Lignocellulosic material may also comprise hemicellulose.

The term "cellulosic" refers to a composition comprising cellulose.

By "dry weight" of biomass is meant the weight of the biomass having all or essentially all water removed. Dry weight is typically measured according to American Society for Testing and Materials (ASTM) Standard E1756-01 (Standard Test Method for Determination of Total Solids in Biomass) or Technical Association of the Pulp and Paper Industry, Inc. (TAPPI) Standard T-412 om-02 (Moisture in Pulp, Paper and Paperboard).

The terms "plasticizer" and "softening agent" refer to materials that cause a reduction in the cohesive intermolecular forces along or between polymer chains. Such materials may act, for example, to decrease crystallinity, or disrupt bonds between lignin and non-lignin carbohydrate fibers (e.g., cellulose or hemicellulose).

The term "saccharification" refers to the production of fermentable sugars from polysaccharides.

The terms "treat" and "pretreat" with respect to biomass are related in the following manner. Biomass is treated with reactant to form a treated biomass product, which may also be referred to as treating to form pretreated biomass or pretreating to form pretreated biomass. The use of "pre" distinguishes the treating of biomass that is prior to saccharification of biomass, The term "pretreated biomass" means biomass that has been subjected to pretreatment prior to saccharification. Pretreatment processes are described in detail below.

"Biomass" refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. According to the invention, biomass may be derived from a single source, or biomass can comprise a mixture derived from more than one source; for example, biomass could comprise a mixture of corn cobs and corn stover or fiber, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure. In one embodiment, biomass that is useful for the invention includes biomass that has a relatively high carbohydrate value, is relatively dense, and/or is relatively easy to collect, transport, store and/or handle. In one embodiment of the invention, biomass that is useful includes corn cobs, corn stover, corn fiber and sugar cane bagasse.

For the purposes of this invention, an "aqueous solution comprising ammonia" refers to the use of ammonia gas ($NH_3$), compounds comprising ammonium ions ($NH_4^+$) such as ammonium hydroxide or ammonium sulfate, compounds that release ammonia upon degradation such as urea, and combinations thereof in an aqueous medium.

An "enzyme consortium" for saccharification is a combination of enzymes that are able to act on a biomass mixture to produce fermentable sugars. Typically, a saccharification enzyme consortium may comprise one or more glycosidases; the glycosidases may be selected from the group consisting of cellulose-hydrolyzing glycosidases, hemicellulose-hydrolyzing glycosidases and starch-hydrolyzing glycosidases. Other enzymes in the saccharification enzyme consortium may include peptidases, lipases, ligninases and feruloyl esterases.

Pretreatment of high concentration biomass with low concentration of aqueous ammonia is described in co-owned and co-pending US patent application US 20070031918A1, which is herein incorporated by reference. Applicants have surprisingly found that inhibitors of saccharification and/or fermentation are released from biomass that is pretreated using the method of US 20070031918A1, while little sugars are released. The sugars that are released are considered insubstantial. For example, an insubstantial sugar loss is about 0.0% up to about 10%, or about 0.01%, 0.02%, 0.04%, 0.06%, 0.07%, or 0.09%. The inhibitors are soluble components of a liquid fraction that can be separated from the pretreated biomass solids. Removing the liquid removes inhibitors and does not substantially reduce sugar yield, thereby producing an improved pretreated biomass product.

Low Aqueous Ammonia Pretreatment

In the low aqueous ammonia pretreatment used in the present method, the concentration of ammonia is minimally a concentration that is sufficient to maintain the pH of the biomass-aqueous ammonia mixture alkaline and maximally less than about 12 weight percent relative to dry weight of biomass. This low concentration of ammonia is sufficient for pretreatment, and the low concentration may also be less than about 10 weight percent relative to dry weight of biomass. A very low concentration of 6 percent ammonia relative to dry weight of biomass, or less, also may be used for pretreatment. By alkaline is meant a pH of greater than 7.0. Particularly suitable is a pH of the biomass-aqueous ammonia mixture that is greater than 8. In one embodiment, ammonia is present at less than about 10 weight percent relative to dry weight of biomass. Particularly suitable is ammonia at less than about 6 weight percent relative to dry weight of biomass.

The aqueous solution comprising ammonia may optionally comprise at least one additional base, such as sodium hydroxide, sodium carbonate, potassium hydroxide, potassium carbonate, calcium hydroxide and calcium carbonate. The at least one additional base may be added in an amount that is combined with ammonium to form an amount of total base that is less than about 20 weight percent relative to dry weight of biomass. Preferably the total second base plus ammonia is in an amount that is less than about 15 weight percent. Additional base(s) may be utilized, for example, to neutralize acids in biomass, to provide metal ions for the saccharification enzymes, or to provide metal ions for the fermentation growth medium.

In the present method, the dry weight of biomass is at an initial concentration of at least about 15% of the weight of the biomass-aqueous ammonia mixture. Typically the dry weight of biomass is at an initial concentration of from at least about 15% to about 80% of the weight of the biomass-aqueous ammonia mixture. In another aspect, the dry weight of biomass is at a concentration of from at least about 15% to about 60% of the weight of the biomass-aqueous ammonia mixture. The percent of biomass in the biomass-aqueous ammonia mixture is kept high to minimize the need for concentration of sugars resulting from saccharification of the pretreated biomass, for use in fermentation. The high biomass concentration also reduces the total volume of pretreatment material, making the process more economical.

The biomass may be used directly as obtained from the source, or energy may be applied to the biomass to reduce the size, increase the exposed surface area, and/or increase the availability of cellulose, hemicellulose, and/or oligosaccharides present in the biomass to ammonia and to saccharification enzymes used to produce sugars from pretreated biomass. Energy means useful for reducing the size, increasing the exposed surface area, and/or increasing the availability of cellulose, hemicellulose, and/or oligosaccharides present in the biomass to ammonia and to saccharification enzymes include, but are not limited to, milling, crushing, grinding, shredding, chopping, disc refining, ultrasound, and microwave. This application of energy may occur before, during or after pretreatment.

Pretreatment of biomass with low aqueous ammonia solution is carried out in any suitable vessel. Typically the vessel is one that can withstand pressure, has a mechanism for heating, and has a mechanism for mixing the contents. Commercially available vessels include, for example, the Zipperclave® reactor (Autoclave Engineers, Erie, Pa.), the Jaygo reactor (described in General Methods; Jaygo Manufacturing, Inc., Mahwah, N.J.), and a steam gun reactor (described in General Methods; Autoclave Engineers, Erie, Pa.). Much larger scale reactors with similar capabilities may be used. Alternatively, the biomass and ammonia solution may be combined in one vessel, then transferred to another reactor. Also biomass may be pretreated in one vessel, then further processed in another reactor such as a steam gun reactor (described in General Methods; Autoclave Engineers, Erie, Pa.). A particularly suitable apparatus that may be used is described in co-owned and co-pending US patent application CL3949, and a system for low ammonia pretreatment using the apparatus of CL3949 is described in co-owned and co-pending US patent application CL3950, both of which are herein incorporated by reference.

Prior to contacting the biomass with an aqueous solution comprising ammonia, vacuum may be applied to the vessel containing the biomass. By evacuating air from the pores of the biomass, better penetration of the ammonia into the biomass may be achieved. The time period for applying vacuum and the amount of negative pressure that is applied to the biomass will depend on the type of biomass and can be determined empirically so as to achieve optimal pretreatment of the biomass (as measured by the production of fermentable sugars following saccharification).

The contacting of the biomass with an aqueous solution comprising ammonia is carried out at a temperature of from about 4° C. to about 200° C. Initial contact of the biomass with ammonia at 4° C., allowing impregnation at this temperature, may increase the efficiency of saccharification over non-pretreated native biomass. In another embodiment, said contacting of the biomass is carried out at a temperature of from about 75° C. to about 150° C. In still another embodiment, said contacting of the biomass is carried out at a temperature of from greater than 90° C. to about 150° C.

The contacting of the biomass with an aqueous solution comprising ammonia is carried out for a period of time up to about 25 hours. Longer periods of pretreatment are possible, however a shorter period of time may be preferable for practical, economic reasons. Typically a period of ammonia contact treatment is about 8 hours or less.

In one embodiment, the pretreatment process may be performed at a relatively high temperature for a relatively short period of time, for example at from about 100° C. to about 150° C. for about 5 min to about 2 hr. In another embodiment, the pretreatment process may be performed at a lower temperature for a relatively long period of time, for example from about 75° C. to about 100° C. for about 2 hr to about 8 hr. In still another embodiment, the pretreatment process may be performed at room temperature (approximately 22-26° C.) for an even longer period of time of about 24 hr. Other temperature and time combinations intermediate to these may also be used.

For the pretreatment process, the "suitable conditions" such as the temperature, time for contact with ammonia, ammonia concentration, concentration of one or more additional bases, biomass concentration, biomass type and biomass particle size are related; thus these variables may be adjusted as necessary to obtain an optimal product.

A plasticizer, softening agent, or combination thereof, such as polyols (e.g., glycerol, ethylene glycol), esters of polyols (e.g., glycerol monoacetate), glycol ethers (e.g., diethylene glycol), acetamide, ethanol, and ethanolamines, may be added in the pretreatment process (i.e., step (a)). A plasticizer may be added as a component of the aqueous ammonia solution, as a separate solution, or as a dry component.

The pretreatment or pretreatment reaction may be performed in any suitable vessel, such as a batch reactor or a continuous reactor. One skilled in the art will recognize that at higher temperatures (above 100° C.), a pressure vessel is required. The suitable vessel may be equipped with a means, such as impellers, for agitating the biomass-aqueous ammonia mixture. Reactor design is discussed in Lin, K.-H., and Van Ness, H. C. (in Perry, R. H. and Chilton, C. H. (eds), Chemical Engineer's Handbook, 5$^{th}$ Edition (1973) Chapter 4, McGraw-Hill, N.Y.). The pretreatment reaction may be carried out as a batch process, or as a continuous process.

It is well known to those skilled in the art that a nitrogen source is required for growth of microorganisms during fermentation; thus the use of ammonia during pretreatment provides a nitrogen source and reduces or eliminates the need to supplement the growth medium used during fermentation with a nitrogen source. If the pH of the pretreatment product exceeds that at which saccharification enzymes are active, or exceeds the range suitable for microbial growth in fermentation, acids may be utilized to reduce pH. The amount of acid used to achieve the desired pH may result in the formation of salts at concentrations that are inhibitory to saccharification enzymes or to microbial growth. In order to reduce the amount of acid required to achieve the desired pH and to reduce the raw material cost of $NH_3$ in the present pretreatment process, ammonia gas may be evacuated from the pretreatment reactor and recycled. Typically, at least a portion of the ammonia is removed, which reduces the pH but leaves some nitrogen that provides this nutrient for use in subsequent fermentation.

Inhibitor Release and Removal

Applicants have surprisingly found that inhibitors are released from biomass reacted with low aqueous ammonia while little sugars are released. The inhibitors are compounds that are detrimental to saccharification and/or fermentation, so it is desirable to reduce the amount of inhibitors present in a pretreated biomass product. The inhibitors were found as solubilized components of a liquid fraction that was present along with the solids following biomass and low aqueous ammonia reaction. This liquid fraction containing inhibitors forms a biomass pretreatment liquor. Removing the biomass pretreatment liquor from the solids results in elimination of the released inhibitors, leaving a solids pretreated biomass product that has reduced inhibitor composition without substantial loss of sugars.

This finding is in contrast to other types of pretreatment processes (such as those described in U.S. Pat. No. 5,705,369, US 2005161038, and US 20040016525) where substantial soluble sugars are released during pretreatment. In these processes, liquid is typically collected as a prehydrolysate containing sugars, and used in fermentation. Thus if inhibitors are also released to the liquid, there is no simple way of removing those inhibitors without also losing the sugars. Methods involving solute separations would be required, which are costly, such as chromatography.

In the present method, liquid in which released inhibitors are solubilized to form the biomass pretreatment liquor is an aqueous component that may be provided in different ways. The aqueous component may be added at any stage of the pretreatment process. The aqueous component may be any water-based component that is added before, during or after adding ammonia. For example, when biomass is pretreated at a solids concentration of about 15 weight percent relative to the weight of the biomass and aqueous ammonia mixture, water may be added to the biomass prior to adding aqueous ammonia or the aqueous ammonia may be dilute enough to reach the final 15 percent biomass concentration. In either case, at this concentration there is likely to be a liquid fraction present in the biomass and aqueous ammonia mixture. Liquid may also be present when biomass is at 20 weight percent or even higher, depending on the type of biomass being pretreated. If steam is added to raise the temperature of the biomass and aqueous ammonia mixture, partial condensation of the steam may provide the added aqueous component. The amount of steam added and amount of condensation leading to a liquid fraction will depend upon factors including the initial temperature of the biomass, aqueous ammonia, and reaction vessel, as well as the final temperature for pretreatment. One skilled in the art will easily determine the contribution of condensed steam under conditions used. Alternatively or in addition, there may be a washing step where, for example, water is added to biomass after reaction with aqueous ammonia and released inhibitors solubilize in this added water.

Solubilized inhibitors may be any compounds detrimental to saccharification and/or fermentation that are released from the low aqueous ammonia treated biomass. A substantial portion of acetic acid, which is an inhibitor of fermentation, and acetamide were present in the biomass pretreatment liquor. These compounds were found in the liquor at a level that represents about 10% of the theoretical amount of acetic acid and acetamide that could potentially be released from the biomass sample. Acetic acid and acetamide are potent growth inhibitors of some types of bacterial cells. For example, acetic acid is an inhibitor of *E. coli*, which is commonly grown in production fermentations. Another example is *Zymomonas*, a bacteria used in fermentation for ethanol production.

The biomass pretreatment liquor may be removed to separate it from the pretreatment solids by methods well known to one skilled in the art, such as by draining, decanting, centrifuging, suctioning, and/or filtering. In addition the biomass may be pressed to release liquor for its removal. When pressing the biomass to remove liquid, it is preferred to not compact the biomass to allow better performance during saccharification.

Following removal of biomass pretreatment liquor, the remaining pretreated biomass product is used in saccharification, or in simultaneous saccharification and fermentation (SSF). In order to obtain sufficient quantities of sugars from biomass, the biomass may be pretreated with an aqueous ammonia solution one time or more than one time. Likewise, a saccharification reaction can be performed one or more times. Both pretreatment and saccharification processes may be repeated if desired to obtain higher yields of sugars. To assess performance of the pretreatment and saccharification processes, separately or together, the theoretical yield of sugars derivable from the starting biomass can be determined and compared to measured yields.

Saccharification:

The improved pretreated biomass prepared according to the present method is then further hydrolyzed in the presence of a saccharification enzyme consortium to release oligosaccharides and/or monosaccharides in a hydrolysate. Saccharification enzymes and methods for biomass treatment are reviewed in Lynd, L. R., et al. (Microbiol. Mol. Biol. Rev. (2002) 66:506-577).

Prior to saccharification, the pretreated biomass may be treated to alter the pH, composition or temperature such that the enzymes of the saccharification enzyme consortium will be active. The pH may be altered through the addition of acids in solid or liquid form. Alternatively, carbon dioxide ($CO_2$), which may be recovered from fermentation, may be utilized to lower the pH. For example, $CO_2$ may be collected from a fermenter and fed into the pretreatment product headspace in the flash tank or bubbled through the pretreated biomass if adequate liquid is present while monitoring the pH, until the desired pH is achieved. The temperature may be brought to a temperature that is compatible with saccharification enzyme activity, as noted below. Any cofactors required for activity of enzymes used in saccharification may be added.

The saccharification enzyme consortium comprises one or more enzymes selected primarily, but not exclusively, from the group "glycosidases" which hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem. (1994) 223:1-5, Eur. J. Biochem. (1995) 232:1-6, Eur. J. Biochem. (1996) 237:1-5, Eur. J. Biochem. (1997) 250:1-6, and Eur. J. Biochem. (1999) 264:610-650, respectively]) of the general group "hydrolases" (EC 3.). Glycosidases useful in the present method can be categorized by the biomass component that they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabinoxylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), and feruloyl esterases (EC 3.1.1.73) to help release polysaccharides from other components of the biomass. It is well known in the art that microorganisms that produce polysaccharide-hydrolyzing enzymes often exhibit an activity, such as cellulose degradation, that is catalyzed by several enzymes or a group of enzymes having different substrate specificities. Thus, a "cellulase" from a microorganism may comprise a group of enzymes, all of which may contribute to the cellulose-degrading activity. Commercial or non-commercial enzyme preparations, such as cellulase, may comprise numerous enzymes depending on the purification scheme utilized to obtain the enzyme. Thus, the saccharification enzyme consortium of the present method may comprise enzyme activity, such as "cellulase", however it is recognized that this activity may be catalyzed by more than one enzyme.

Saccharification enzymes may be obtained commercially, such as Spezyme® CP cellulase (Genencor International, Rochester, N.Y.) and Multifect® xylanase (Genencor). In addition, saccharification enzymes may be produced biologically, including using recombinant microorganisms.

One skilled in the art would know how to determine the effective amount of enzymes to use in the consortium and adjust conditions for optimal enzyme activity. One skilled in the art would also know how to optimize the classes of enzyme activities required within the consortium to obtain optimal saccharification of a given pretreatment product under the selected conditions.

Preferably the saccharification reaction is performed at or near the temperature and pH optima for the saccharification enzymes. The temperature optimum used with the saccharification enzyme consortium in the present method ranges from about 15° C. to about 100° C. In another embodiment, the temperature optimum ranges from about 20° C. to about 80° C. The pH optimum can range from about 2 to about 11. In another embodiment, the pH optimum used with the saccharification enzyme consortium in the present method ranges from about 4 to about 10.

The saccharification can be performed for a time of about several minutes to about 120 hr, and preferably from about several minutes to about 48 hr. The time for the reaction will depend on enzyme concentration and specific activity, as well as the substrate used and the environmental conditions, such as temperature and pH. One skilled in the art can readily determine optimal conditions of temperature, pH and time to be used with a particular substrate and saccharification enzyme(s) consortium.

The saccharification can be performed batch-wise or as a continuous process. The saccharification can also be performed in one step, or in a number of steps. For example, different enzymes required for saccharification may exhibit different pH or temperature optima. A primary treatment can be performed with enzyme(s) at one temperature and pH, followed by secondary or tertiary (or more) treatments with different enzyme(s) at different temperatures and/or pH. In addition, treatment with different enzymes in sequential steps may be at the same pH and/or temperature, or different pHs and temperatures, such as using hemicellulases stable and more active at higher pHs and temperatures followed by cellulases that are active at lower pHs and temperatures.

The degree of solubilization of sugars from biomass following saccharification can be monitored by measuring the release of monosaccharides and oligosaccharides. Methods to measure monosaccharides and oligosaccharides are well known in the art. For example, the concentration of reducing sugars can be determined using the 1,3-dinitrosalicylic (DNS) acid assay (Miller, G. L., Anal. Chem. (1959) 31:426-428). Alternatively, sugars can be measured by HPLC using an appropriate column as described herein in the General Methods section.

Fermentation

Fermentable sugars released from biomass can be used by suitable microorganisms to produce target chemicals. Following saccharification, but prior to fermentation, the saccharification mixture may be concentrated by evaporation, for example, to increase the concentration of fermentable sugars. Optionally, liquid in the saccharification product may be separated from solids in a batch or continuous method. Optionally, the liquid or the entire saccharification product may be sterilized prior to fermentation. Depending on the microorganism(s) used during fermentation and the pH used during saccharification, the pH may be adjusted to that suitable for fermentation. In addition, the saccharification mixture may be supplemented with additional nutrients required for microbial growth. Supplements may include, for example, yeast extract, specific amino acids, phosphate, nitrogen sources, salts, and trace elements. Components required for production of a specific product made by a specific biocatalyst may also be included, such as an antibiotic to maintain a plasmid or a cofactor required in an enzyme catalyzed reaction. Also additional sugars may be included to increase the total sugar concentration. The saccharification mixture may be used as a component of a fermentation broth, for example, making up between about 100% and about 10% of the final medium Temperature and/or headspace gas may also be adjusted, depending on conditions useful for the fermentation microorganism(s). Fermentation may be aerobic or anaerobic. Fermentation may occur subsequent to saccharification, or may occur concurrently with saccharification by simultaneous saccharification and fermentation (SSF). SSF can keep the sugar levels produced by saccharification low, thereby reducing potential product inhibition of the saccharification enzymes, reducing sugar availability for contaminating microorganisms, and improving the conversion of pretreated biomass to monosaccharides and/or oligosaccharides.

Target chemicals that may be produced by fermentation using biocatalysts include, for example, acids, alcohols, alkanes, alkenes, aromatics, aldehydes, ketones, biopolymers, proteins, peptides, amino acids, vitamins, antibiotics, and pharmaceuticals. Alcohols include, but are not limited to methanol, ethanol, propanol, isopropanol, butanol, ethylene glycol, propanediol, butanediol, glycerol, erythritol, xylitol, and sorbitol. Acids include acetic acid, lactic acid, propionic acid, 3-hydroxypropionic, butyric acid, gluconic acid, itaconic acid, citric acid, succinic acid and levulinic acid. Amino acids include glutamic acid, aspartic acid, methionine, lysine, glycine, arginine, threonine, phenylalanine and tyrosine. Additional target chemicals include methane, ethylene, acetone and industrial enzymes.

The fermentation of sugars to target chemicals may be carried out by one or more appropriate biocatalysts in single or multistep fermentations. Biocatalysts may be microorganisms selected from bacteria, filamentous fungi and yeast. Biocatalysts may be wild type microorganisms or recombinant microorganisms, and include *Escherichia, Zymomonas, Saccharomyces, Candida, Pichia, Streptomyces, Bacillus, Lactobacillus,* and *Clostridium*. In another embodiment, biocatalysts may be selected from the group consisting of recombinant *Escherichia coli, Zymomonas mobilis, Bacillus stearo-*

*thermophilus, Saccharomyces cerevisiae, Clostridia thermocellum, Thermoanaerobacterium saccharolyticum,* and *Pichia stipitis*

Many biocatalysts used in fermentation to produce target chemicals have been described and others may be discovered, produced through mutation, or engineered through recombinant means. Any biocatalyst that uses fermentable sugars produced from saccharification of pretreated biomass using the present system may be used to make the target chemical(s) that it is known to produce by fermentation.

Particularly of interest are biocatalysts that produce biofuels including ethanol and butanol. For example, fermentation of carbohydrates to acetone, butanol, and ethanol (ABE fermentation) by solventogenic Clostridia is well known (Jones and Woods (1986) Microbiol. Rev. 50:484-524). A fermentation process for producing high levels of butanol, also producing acetone and ethanol, using a mutant strain of *Clostridium acetobutylicum* is described in U.S. Pat. No. 5,192,673. The use of a mutant strain of *Clostridium beijerinckii* to produce high levels of butanol, also producing acetone and ethanol, is described in U.S. Pat. No. 6,358,717. Co-owned and co-pending patent applications WO 2007/041269 and WO 2007/050671, which are herein incorporated by reference, disclose the production of 1-butanol and isobutanol, respectively, in genetically engineered microbial hosts. Co-owned and co-pending U.S. patent applications No. 11/741,892 and No. 11/741,916, which are herein incorporated by reference, disclose the production of 2-butanol in genetically engineered microbial hosts. Isobutanol, 1-butanol or 2-butanol may be produced from fermentation of hydrolysate produced using the present system by a microbial host following the disclosed methods.

Genetically modified strains of *E. coli* have also been used as biocatalysts for ethanol production (Underwood et al., (2002) Appl. Environ. Microbio. 68:6263-6272). A genetically modified strain of *Zymomonas mobilis* that has improved production of ethanol is described in US 2003/0162271 A1. A further engineered ethanol-producing strain of *Zymomonas mobilis* and its use for ethanol production are described in co-owned and co-pending U.S. patent applications 60/847,813 and 60/847,856, respectively, which are herein incorporated by reference. Ethanol may be produced from fermentation of hydrolysate produced using the present system by *Zymomonas mobilis* following the disclosed methods. Saccharification of pretreated biomass which had pretreatment liquor containing inhibitors removed, to fermentable sugars followed by fermentation of the sugars to a target chemical is exemplified in Example 4 herein for the production of ethanol from pretreated corn cobs using *Z. mobilis* as the biocatalyst for the fermentation of sugars to ethanol.

Lactic acid has been produced in fermentations by recombinant strains of *E. coli* (Zhou et al., (2003) Appl. Environ. Microbiol. 69:399-407), natural strains of *Bacillus* (US20050250192), and *Rhizopus oryzae* (Tay and Yang (2002) Biotechnol. Bioeng. 80:1-12). Recombinant strains of *E. coli* have been used as biocatalysts in fermentation to produce 1,3 propanediol (U.S. Pat. No. 6,013,494, U.S. Pat. No. 6,514,733), and adipic acid (Niu et al., (2002) Biotechnol. Prog. 18:201-211). Acetic acid has been made by fermentation using recombinant *Clostridia* (Cheryan et al., (1997) Adv. Appl. Microbiol. 43:1-33), and newly identified yeast strains (Freer (2002) World J. Microbiol. Biotechnol. 18:271-275). Production of succinic acid by recombinant *E. coli* and other bacteria is disclosed in U.S. Pat. No. 6,159,738, and by mutant recombinant *E. coli* in Lin et al., (2005) Metab. Eng. 7:116-127). Pyruvic acid has been produced by mutant *Torulopsis glabrata* yeast (Li et al., (2001) Appl. Microbiol. Technol. 55:680-685) and by mutant *E. coli* (Yokota et al., (1994) Biosci. Biotech. Biochem. 58:2164-2167). Recombinant strains of *E. coli* have been used as biocatalysts for production of para-hydroxycinnamic acid (US20030170834) and quinic acid (US20060003429).

A mutant of *Propionibacterium acidipropionici* has been used in fermentation to produce propionic acid (Suwannakham and Yang (2005) Biotechnol. Bioeng. 91:325-337), and butyric acid has been made by *Clostridium tyrobutyricum* (Wu and Yang (2003) Biotechnol. Bioeng. 82:93-102). Propionate and propanol have been made by fermentation from threonine by *Clostridium* sp. strain 17cr1 (Janssen (2004) Arch. Microbiol. 182:482-486). A yeast-like *Aureobasidium pullulans* has been used to make gluconic acid (Anantassiadis et al., (2005) Biotechnol. Bioeng. 91:494-501), by a mutant of *Aspergillis niger* (Singh et al., (2001) Indian J. Exp. Biol. 39:1136-43). 5-keto-D-gluconic acid was made by a mutant of *Gluconobacter oxydans* (Elfari et al., (2005) Appl Microbiol. Biotech. 66:668-674), itaconic acid was produced by mutants of *Aspergillus terreus* (Reddy and Singh (2002) Bioresour. Technol. 85:69-71), citric acid was produced by a mutant *Aspergillus niger* strain (Ikram-Ul-Haq et al., (2005) Bioresour. Technol. 96:645-648), and xylitol was produced by *Candida guilliermondii* FTI 20037 (Mussatto and Roberto (2003) J. Appl. Microbiol. 95:331-337). 4-hydroxyvalerate-containing biopolyesters, also containing significant amounts of 3-hydroxybutyric acid 3-hydroxyvaleric acid, were produced by recombinant *Pseudomonas putida* and *Ralstonia eutropha* (Gorenflo et al., (2001) Biomacromolecules 2:45-57). L-2,3-butanediol was made by recombinant *E. coli* (Ui et al., (2004) Lett. Appl. Microbiol. 39:533-537).

Production of amino acids by fermentation has been accomplished using auxotrophic strains and amino acid analog-resistant strains of *Corynebacterium, Brevibacterium,* and *Serratia*. For example, production of histidine using a strain resistant to a histidine analog is described in Japanese Patent Publication No. 56008596 and using a recombinant strain is described in EP 136359. Production of tryptophan using a strain resistant to a tryptophan analog is described in Japanese Patent Publication Nos. 47004505 and 51019037. Production of isoleucine using a strain resistant to an isoleucine analog is described in Japanese Patent Publication Nos. 47038995, 51006237, 54032070. Production of phenylalanine using a strain resistant to a phenylalanine analog is described in Japanese Patent Publication No. 56010035. Production of tyrosine using a strain requiring phenylalanine for growth, resistant to tyrosine (Agr. Chem. Soc. Japan 50 (1) R79-R87 (1976), or a recombinant strain (EP263515, EP332234), and production of arginine using a strain resistant to an L-arginine analog (Agr. Biol. Chem. (1972) 36:1675-1684, Japanese Patent Publication Nos. 54037235 and 57150381) have been described. Phenylalanine was also produced by fermentation in *Eschericia coli* strains ATCC 31882, 31883, and 31884. Production of glutamic acid in a recombinant coryneform bacterium is described in U.S. Pat. No. 6,962,805. Production of threonine by a mutant strain of *E. coli* is described in Okamoto and Ikeda (2000) J. Biosci Bioeng. 89:87-79. Methionine was produced by a mutant strain of *Corynebacterium lilium* (Kumar et al, (2005) Bioresour. Technol. 96: 287-294).

Useful peptides, enzymes, and other proteins have also been made by biocatalysts (for example, in U.S. Pat. No. 6,861,237, U.S. Pat. No. 6,777,207, U.S. Pat. No. 6,228,630).

The method of the present invention may also be used in the production of 1,3-propanediol from biomass. Recombinant strains of *E. coli* have been used as biocatalysts in fermentation to produce 1,3 propanediol (U.S. Pat. No. 6,013,494, U.S. Pat. No. 6,514,733). Biomass pretreated using the present system may be saccharified; following saccharification, *E. coli* is used to produce 1,3-propanediol as described in Example 10 of co-owned and co-pending U.S. application Ser. No. 11/403,087, which is herein incorporated by reference.

Target chemicals produced in fermentation by biocatalysts may be recovered using various methods known in the art. Products may be separated from other fermentation components by centrifugation, filtration, microfiltration, and nanofiltration. Products may be extracted by ion exchange, solvent extraction, or electrodialysis. Flocculating agents may be used to aid in product separation. As a specific example, bioproduced 1-butanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the 1-butanol may be isolated from the fermentation medium using methods such as distillation, azeotropic distillation, liquid-liquid extraction, adsorption, gas stripping, membrane evaporation, or pervaporation. Purification of 1,3-propanediol from fermentation media may be accomplished, for example, by subjecting the reaction mixture to extraction with an organic solvent, distillation, and column chromatography (U.S. Pat. No. 5,356,812). A particularly good organic solvent for this process is cyclohexane (U.S. Pat. No. 5,008,473). Amino acids may be collected from fermentation medium by methods such as ion-exchange resin adsorption and/or crystallization.

EXAMPLES

General Methods and Materials

The following abbreviations are used:

"HPLC" is High Performance Liquid Chromatography, "C" is Centigrade, "kPa" is kiloPascal, "m" is meter, "mm" is millimeter, "kW" is kilowatt, "µm" is micrometer, "µL" is microliter, "mL" is milliliter, "L" is liter, "min" is minute, "mM" is millimolar, "cm" is centimeter, "g" is gram, "kg" is kilogram, "wt" is weight, "hr" is hour, "temp" or "T" is temperature, "theoret" is theoretical, "pretreat" is pretreatment, "DWB" is dry weight of biomass, "ASME" is the American Society of Mechanical Engineers, "s.s." is stainless steel.

Sulfuric acid, ammonium hydroxide, acetic acid, acetamide, yeast extract, glucose, xylose, sorbitol, $MgSO_4.7H_2O$, phosphoric acid and citric acid were obtained from Sigma-Aldrich (St. Louis, Mo.).

Jaygo Reactor

The Jaygo reactor is a 130-liter (approximately 51 cm diameter×91 cm length), horizontal paddle type reactor (Jaygo Manufacturing, Inc., Mahwah, N.J.) fabricated of Hastelloy® C-22 alloy. The reactor is equipped with a steam jacket capable of heating to approximately 177° C. (862 kPa). Direct steam injection is also used to rapidly bring the biomass up to pretreatment temperature. Steam pressure is adjusted and controlled to maintain the desired pretreatment temperature. Numerous ports allow injection of other solvents and hot liquids.

Large Barrel Piston Reactor

A large barrel piston reactor (ASME code stamped) was constructed that consisted of a 5.1 cm×68.6 cm stainless steel barrel equipped with a piston, oriented horizontally. The piston was sealed to the barrel with four O-rings and was pressurized with nitrogen on the backside of the piston during the discharge stroke. The 68.6 cm barrel was equipped with eight multiple use ports, 4 each along the top and bottom surfaces, allowing application of vacuum, injection of aqueous ammonia, injection of steam, and insertion of thermocouples for measurement of temperature inside the barrel. The reactor barrel was equipped with a steam jacket for even heating of the barrel. The reactor barrel was directly attached to a 15.2 cm×61 cm stainless steel flash tank, oriented vertically. The barrel was isolated from the flash tank by a conical nozzle and seat end shearing valve arrangement. The diameter of the end valve shearing die was 3.5 cm. The backpressure on the conical nozzle and seat was adjustable, with most tests performed using ~138 kPa (gauge pressure) of backpressure into a 10.2 cm diameter air cylinder connected to the cone of the end shear valve. The cone of the end shearing valve could move back up to 1.6 cm to allow discharge of particles in the flash tank. An elbow at the outlet of the end shear valve directed the pretreated solids down into the bottom of the flash tank where the solids were easily removed by unbolting a domed end flange in the bottom of the tank. An upper domed flange to the flash tank incorporated a special outlet fitting with slots machined at right angles to the axis of the flash tank, which caused released vapors to travel around a corner path to an exit fitting, helping to prevent carry-over of entrained biomass particles and water droplets into a vent condenser. Three electrical band heaters (set at 60° C.) and insulation were added along the flash tank to allow hot pretreated solids to flash into a heated vessel, better simulating a commercial scale process.

Fed-Batch Saccharification Reactor

This reactor is described in more detail in co-owned and co-pending US patent application CL3873, which is herein incorporated by reference. The fed-batch saccharification reactor is a 15-L fermentor (B. Braun Biotech International, Allentown, Pa.) controlled by a BioStat ED data control unit and associated control module containing a circulating pump, acid and base pumps, solenoid valves, heat exchangers for temperature control, steam supply, process water, air supply control valves and filtration, and back pressure control valves and exhaust filters. The fermentor was equipped with two 11.4 cm diameter three-blade high efficiency Ligntnin A-310 impellers. The bottom impeller was located 7.6 cm from the reactor bottom (it could not be located any closer due to the presence of a large seal arrangement near the bottom of the shaft for the bottom-drive shaft penetration) and the upper impeller was located 22.9 cm from the reactor bottom. The fermentor vessel has a diameter of 19.0 cm and a maximum height of 55.9 cm. Four removable baffles were installed, each of which has a width of 1.6 cm and a length of 48.3 cm and extended from the vessel bottom to within ~7.6 cm of the top. Plumbed into the top and bottom ports on the fermenter system was a pump-around loop consisting of an APV lobe pump (model M1/028/06), 1½-in (3.81 cm) flexible hoses and a Teflon sight flow indicator. The pump around loop was isolated from the fermentation vessel with 1½-in (3.81 cm) Valmicro and SVF full port ball valves with $CF_8M$ bodies, 316 s.s. balls, and PTFE seats. Additionally, a V-port shear valve (Triac Controls) was located downstream of the lobe pump, prior to the ball valve isolating the pump from the top port of the fermentor. During the recirculation cycles, this valve was gradually closed to up to 600 to provide greater shearing of the recirculating pretreated solids.

Analytical Methods

Glucose and Xylose Quantitation in Solids

The amount of glucose and xylose in each starting biomass sample was determined using methods well known in the art, such as ASTM E1758-01 "Standard method for the determination of carbohydrates by HPLC".

Measurement of Soluble Sugar, Acetamide, Lactic Acid and Acetic Acid Content

Soluble sugars (glucose, cellobiose, xylose, galactose, arabinose and mannose), acetic acid and ethanol in saccharification liquor or fermentation broth were measured by HPLC (Agilent Model 1100, Agilent Technologies, Palo Alto, Calif.) using Bio-Rad HPX-87P and Bio-Rad HPX-87H columns (Bio-Rad Laboratories, Hercules, Calif.) with appropriate guard columns. The sample pH was measured and adjusted to 5-6 with sulfuric acid if necessary. The sample was then passed through a 0.2 μm syringe filter directly into an HPLC vial. The HPLC run conditions were as follows:

HPX-87P (for carbohydrates):
  Injection volume: 10-50 μL, dependent on concentration and detector limits
  Mobile phase: HPLC grade water, 0.2 μm filtered and degassed
  Flow rate: 0.6 mL/minute
  Column temperature: 80-85° C., guard column temperature <60° C.
  Detector temperature: as close to main column temperature as possible
  Detector: refractive index
  Run time: 35 minute data collection plus 15 minute post run (with possible adjustment for later eluting compounds)

Biorad Aminex HPX-87H (for carbohydrates, acetic acid and ethanol)
  Injection volume: 5-10 μL, dependent on concentration and detector limits
  Mobile phase: 0.01N Sulfuric acid, 0.2 μm filtered and degassed
  Flow rate: 0.6 mL/minute
  Column temperature: 55° C.
  Detector temperature: as close to column temperature as possible
  Detector: refractive index
  Run time: 25-75 minute data collection After the run, concentrations in the sample were determined from standard curves for each of the compounds.

Example 1

Little Solubilization of Sugars after Low Temperature Pretreatment

Whole or fractured corn cobs (approximately 13 kg, dry weight basis) were loaded into the Jaygo reactor. Cobs were fractured by passing through the disk refiner (General Methods) equipped with plates C-2975. Resulting fractured cobs were passed through a 1.27 cm screen. Any pieces retained were passed through the disk refiner again with a 0.5 cm smaller gap. A vacuum was applied to the reactor, and dilute ammonium hydroxide solution was injected to give the final desired ammonia concentration (2% or 6% wt $NH_3$/wt dry biomass) and concentration of dry biomass (30% or 40% wt dry biomass/wt total biomass-aqueous ammonia mixture). In the case of whole cobs, the initial ammonia concentration was 6% (wt/wt dry biomass) and dry biomass concentration was 40%. In the case of fractured cobs, the initial ammonia concentration was 2% (wt/wt dry biomass) and dry biomass concentration was 30%. The vacuum was relieved and steam was applied to the jacket to heat the cobs while soaking to a temperature of 93° C. for the whole cob sample and 85° C. for fractured cob samples. Short periods of increased agitator speeds (up to 96 rpm) were applied in an effort to increase the heating rate. The soaked cobs were held at temperature for 8 hr for whole cobs and 4 hr for fractured cobs with constant mixing at 32 rpm, then allowed to cool overnight with continued mixing. Prior to removing pretreated biomass from the reactor, the reactor was put under vacuum at 90° C. to strip ammonia out of the pretreated biomass.

The composition of the solid and liquid phases of the whole cob pretreated biomass mixture was analyzed as described in General Methods and results are given in Table 1. Amounts are given as % of theoretical amounts in the starting biomass, with acetic acid and acetamide together corresponding to acetyl in the biomass. Glucose and xylose remained largely in the solids (in cellulose and hemicellulose, respectively), with only small amounts of soluble oligomers measured in the liquid. All of the feedstock acetyl was found in the liquid phase as either acetic acid or acetamide.

TABLE 1

Partitioning of different feedstock components to solid or liquid phase after low temperature pretreatment of whole cobs.

| Component | Solid phase: % theoretical feedstock value | Liquid phase: % theoretical feedstock value | | | |
|---|---|---|---|---|---|
| | | Monomer sugars | Oligomer sugars | Acetic acid | Acetamide |
| Glucose | 99 | 0 | 1 | — | — |
| Xylose | 83 | 0 | 7*1 | — | — |
| Acetyl | 0 | — | — | 56 | 44 |

*totals may not be 100 due to assay sensitivity level

The composition of the solid and liquid phases of the fractured cob pretreated biomass mixture was analyzed as described in General Methods and results are given in Table 2. Amounts are given as % of theoretical amounts in the starting biomass, with acetic acid and acetamide together corresponding to acetyl in the biomass. As with the whole cob pretreated biomass, glucose and xylose remained largely in the solids (in cellulose and hemicellulose, respectively), with only small amounts of soluble oligomers measured in the liquid. Also all of the feedstock acetyl was found in the liquid phase as either acetic acid or acetamide.

TABLE 2

Partitioning of different feedstock components to solid or liquid phase after low temperature pretreatment of fractured cobs.

| Component | Solid phase: % theoretical feedstock value | Liquid phase: % theoretical feedstock value | | | |
|---|---|---|---|---|---|
| | | Monomer sugars | Oligomer sugars | Acetic acid | Acetamide |
| Glucose | 97 | 2 | 2* | — | — |
| Xylose | 92 | — | 1* | — | — |
| Acetyl | 0 | — | — | 81 | 9* |

*totals may not be 100 due to assay sensitivity level

Example 2

Little Solubilization of Sugars after High Temperature Pretreatment

Fractured corn cobs (13 kg, dry basis), prepared as described in Example 1, were loaded into the Jaygo reactor. After pulling a vacuum on the reactor, ammonium hydroxide solution of the proper strength to give 2% ammonia (wt/wt dry biomass) and 30% dry weight of biomass concentration was pumped into the reactor with 32 rpm mixing at room temperature. The contents of the reactor were then heated to 95° C. using low-pressure jacket steam. Once the reactor reached 95° C., direct steam injection was used to heat the contents of the reactor to 145° C. When the reactor reached 145° C., the reactor contents were held at that temperature for 20 minutes using jacket steam and some direct steam injection. After 20 minutes, a vacuum was pulled on the vent to the reactor and the shredder motor was turned on for 5 minutes. After 1 hr the cooling water to the jacket was turned on. The contents of the Jaygo reactor were cooled to between 33° C. and 37° C.; then $CO_2$ was used to pressurize the reactor to 138 kPa. The pressurized $CO_2$ atmosphere was maintained for 30 min. The final temperature of the reactor contents was between 27° C. to 31° C. The pH of the soaked/pretreated biomass was approximately 7.5.

The composition of the solid and liquid phases of the pretreated biomass mixture was analyzed as described in General Methods and results are given in Table 3. Amounts are given as % of theoretical amounts in the starting biomass, with acetic acid and acetamide together corresponding to acetyl in the biomass. As with the low temperature pretreated biomass in Example 1, glucose and xylose remained largely in the solids (in cellulose and hemicellulose, respectively), with only small amounts of soluble oligomers measured in the liquid. Also all of the feedstock acetyl was found in the liquid phase as either acetic acid or acetamide.

TABLE 3

Partitioning of different feedstock components to solid or liquid phase after high temperature pretreatment of fractured cobs.

| Component | Solid phase: % theoretical feedstock value | Liquid phase: % theoretical feedstock value | | | |
|---|---|---|---|---|---|
| | | Monomer sugars | Oligomer sugars | Acetic acid | Acetamide |
| Glucose | 100 | 0 | 2* | — | — |
| Xylose | 93 | 0 | 2* | — | — |
| Acetyl | 0 | — | — | 90 | 9* |

*totals may not be 100 due to assay sensitivity level

Example 3

Pretreatment Liquors Contain Fermentation Inhibitors

A series of pretreatments was carried out in the large barrel piston reactor (described in General Methods) as follows. Steam was added to the jacket of the barrel to preheat the barrel of the large barrel piston reactor (described in General Methods) to ~130° C. The flash receiver was preheated to ~60° C. with band heaters. Whole corn cobs were processed with a jaw crusher (2.2 kW motor) with a jaw spacing of approximately 0.95 cm, followed by a delumper (1.5 kW motor, Franklin Miller Inc., Livingston, N.J.), followed by screening with a Sweco screen equipped with a 1.9 cm U.S. Standard screen to fracture the whole cobs into smaller pieces. These fractured cobs (175 g, dry weight basis) were loaded into the large barrel reactor by hand placing of cobs into the end of the reactor with the piston removed. The piston was replaced to plug the end. A vacuum was applied to the reactor vessel and to the flash receiver to bring the pressure down <10 kPa, and dilute ammonium hydroxide solution was injected into the reactor to give an ammonia concentration of 6 g/100 g dry weight of biomass and a dry weight of biomass concentration of 45 g/100 g total biomass-aqueous ammonia mixture. Once the ammonia was charged, steam was injected into the reactor to bring the temperature to 145° C. The mixture was held at this temperature for 10 minutes by monitoring the temperature and adding steam as necessary and then discharged into the preheated flash tank by activating the piston. Vacuum was pulled on the flash tank until the flash receiver reached ~59° C. For series A, 12 such pretreatments were carried and for series B, 13 such pretreatments were carried out. Solids were harvested by removing the bottom of the flash tank. Any excess liquid was drained from the solids, and all the liquid collected from each pretreatment series was pooled together. This liquid was analyzed for sugar content, acetic acid and acetamide as described in General Methods. The liquid was very low in sugars while containing more acetic acid and acetamide, as shown in Tables 4 and 5.

TABLE 4

Sugar removed in pretreatment liquors.

| Pretreatment series | Monomer Glucose: % theoretical | Total Glucose: % theoretical | Monomer Xylose: % theoretical | Total Xylose: % theoretical |
|---|---|---|---|---|
| A | 0.02% | 0.15% | 0 | 0.12% |
| B | 0 | 0.13% | 0 | 0.11% |

TABLE 5

Acetic acid and acetamide removed in pretreatment liquors.

| Pretreatment series | Acetic Acid % theoretical | Acetamide % theoretical |
|---|---|---|
| A | 6.2% | 1.8% |
| B | 10.2% | 2.7% |

Example 4

Production of Ethanol using Saccharification Hydrolysate from Pretreated Biomass with Inhibitors in Liquid Removed Steam was added to the jacket of the barrel to preheat the barrel of the large barrel piston reactor (described in General Methods) to ~130° C. The flash receiver was preheated to ~60° C. with band heaters. Fractured cobs were prepared as follows. Whole corn cobs were processed with a jaw crusher (2.2 kW motor) with a jaw spacing of approximately 0.95 cm, followed by a delumper (1.5 kW motor, Franklin Miller Inc., Livingston, N.J.), followed by screening with a Sweco screen equipped with a 1.9 cm U.S. Standard screen to fracture the whole cobs into smaller pieces. These processed cobs (175 g, dry weight basis) were loaded into the large barrel piston reactor by hand placing of cobs into the end of the reactor with the piston removed. The piston was replaced to plug the end. A vacuum was applied to the reactor vessel and to the flash receiver to bring the pressure down <10 kPa, and dilute ammonium hydroxide solution was injected into the reactor to give an ammonia concentration of 6 g/100 g dry weight of biomass and a dry weight of biomass concentration of 45 g/100 g total biomass-aqueous ammonia mixture. Once the ammonia was charged, steam was injected into the reactor to bring the temperature to 145° C. The mixture was held at this temperature for 10 minutes by monitoring the temperature and adding steam as necessary and then discharged into the preheated flash tank by activating the piston. Vacuum was pulled on the flash tank until the flash receiver reached ~59° C. Upon harvest from the flash receiver, free liquid was separated from the pretreated solids and not added back for saccharification. A total of 17 such pretreatments were carried out. Pretreated cobs from 4 pretreatments were pooled for saccharification to provide initial hydrolysate for the fed-batch saccharification. Pretreated cobs from the remaining 13 runs were pooled for use in the fed-batch saccharification.

To start the fed-batch saccharification, the fed-batch saccharification reactor described in General Methods was first loaded with hydrolysate to fill the reactor volume up to the bottom of the first impeller. This hydrolyzate was prepared by saccharifying pretreated cobs in 2.8-L shake flasks. These shake flasks were loaded with 465 g pretreated solids, 1000 ml Di water, and enzymes at 28.4 mg Spezyme® CP/g cellulose and 4.2 mg active protein/g cellulose hemicellulase enzyme consortium (Diversa, San Diego, Calif.) comprising β-glucosidase, xylanase, β-xylosidase and arabinofuranosidase. Prior to enzyme addition, pH was adjusted to 5 with 8.5% $H_3PO_4$. The shake flasks were maintained at 50° C. and 150 rpm in a rotary shaker for 48 hr, at which time the hydrolysate was loaded into the fed-batch reactor.

Once the initial hydrolysate was loaded, the first aliquot of the pretreated biomass-ammonia mixture (~700 g) was added to the reactor. The pH was maintained at a setpoint of 5.5 by addition of 8.5% $H_3PO_4$. Once the pH readjusted to the setpoint, 28.4 mg of Spezyme® CP/g cellulose and 4.2 mg active protein/g cellulose of hemicellulase enzyme consortium (Diversa) comprising β-glucosidase, xylanase, β-xylosidase and arabinofuranosidase were added. Additional aliquots of the pretreated biomass-ammonia mixture, Spezyme® CP cellulase and hemicellulase enzyme consortium were added at t=4, 8, 12, 22, 26, 30 and 34 hr. The pump around loop was generally started about 1 hr after enzyme addition and was run for about 1 hr up through the 22 hr solids addition. After the 26 hr and 30 hr additions, the pump was started about 50 min after enzyme addition and run for 30 minutes. After the 34 hr addition, the pump was started ~3 hr after enzyme addition and run for 30 minutes. The pump was also run for 30 minutes at t=29, 33, 47 and 49 hr. Total saccharification time was 120 hr. At this time, hydrolysate contained ~60 g/L monomer glucose, 25 g/L monomer xylose and 10 g/L acetic acid.

This hydrolyzate was used for fermentation of *Zymomonas mobilis* strains ZW800 or ZW658 (ATCC # PTA-7858). ZW658 is a strain of *Zymomonas mobilis* that has been engineered for xylose fermentation to ethanol and is described in co-owned and co-pending U.S. Patent Application 60/847,813, which is herein incorporated by reference. ZW658 was constructed by integrating two operons, $P_{gap}$xylAB and $P_{gap}$taltkt, containing four xylose-utilizing genes encoding xylose isomerase, xylulokinase, transaldolase and transketolase, into the genome of ZW1 (ATCC #31821) via sequential transposition events, and followed by adaptation on selective media containing xylose. ZW800 is the ZW658 strain with the gene encoding glucose-fructose oxidoreductase inactivated, which is also described in co-owned and co-pending U.S. Patent Application 60/847,813.

Fermentations were carried out in sterilized 1-liter fermentors (BIOSTAT® B-DCU system, Sartorius BBI System Inc., Bethlehem, Pa., USA) with 500 ml initial working volume. Inoculum was added to the fermentor at a level of 10% (v/v) such that the $OD_{600}$-1 in the broth after addition. Hydrolysate was present at 80% or 40% (v/v), with the balance as water. Additional glucose and xylose were added to bring final concentrations in the broth to 92 g/L and 82 g/L, respectively. Broth was also supplemented with 10 mM sorbitol and 1 g/L $MgSO_4.7H_2O$. Fermentation was carried out for 72 hr at 33° C., pH 5.8 with 150 rpm agitation. Final ethanol titers for the ZW800 strain were 8 g/L in the 40% hydrolysate and 7 g/L in the 80% hydrolysate. For ZW658, the final ethanol titers were 8 g/L in 40% hydrolyzate and 6.5 g/L in 80% hydrolyzate.

What is claimed is:

1. A method for producing saccharification hydrolysate from biomass comprising:
    a) providing biomass;
    b) pretreating said biomass by contacting said biomass under suitable conditions with an aqueous solution comprising ammonia to form a biomass-aqueous ammonia mixture, wherein the ammonia is present at a concentration at least sufficient to maintain alkaline pH of the biomass-aqueous ammonia mixture but wherein said ammonia is present at 12 weight percent or less relative to dry weight of biomass, and further wherein the dry weight of biomass is at a solids concentration of 15 weight percent or more relative to the weight of the biomass-aqueous ammonia mixture whereby a pretreated biomass solids product and a biomass pretreatment liquor comprising one or more saccharification or fermentation inhibitor compounds is formed;
    c) removing said biomass pretreatment liquor; and
    d) saccharifying the pretreated biomass solids product of step (b) to form saccharification hydrolysate containing fermentable sugars.

2. The method of claim 1, further comprising adding an additional aqueous component in one or more of the following ways:
    i) prior to step (b)
    ii) as an additional component in step (b); or
    iii) after step(b) as a wash step.

3. The method of claim 2 wherein said additional aqueous component is selected from the group consisting of steam, water, and buffer.

4. The method of claim 3, wherein the aqueous component is steam and is added as an additional component in step (b) wherein the steam partially condenses during pretreatment to form part of the biomass pretreatment liquor.

5. The method of claim 1, further comprising fermenting the sugars of claim 1 to produce a target chemical.

6. The method of claim 1 wherein the method of liquor removal is selected from the group consisting of draining, decanting, filtering, centrifuging, and pressing.

7. The method of claim 1 wherein the pH of the biomass-aqueous ammonia mixture is greater than 8.

8. The method of claim 1 wherein vacuum is applied to the biomass prior to contacting the biomass with an aqueous solution comprising ammonia.

9. The method of claim 1 wherein said dry weight of biomass is at a high solids concentration of from at least about 15% to about 80% relative to the weight of the biomass-aqueous ammonia mixture.

10. The method of claim 9 wherein said dry weight of biomass is at a high solids concentration of from at least about 15% to about 60% relative to the weight of the biomass-aqueous ammonia mixture.

11. The method of claim 1 wherein said ammonia is present at less than about 10 weight percent relative to dry weight of biomass.

12. The method of claim 11 wherein said ammonia is present at about 6% or less weight percent relative to dry weight of biomass.

13. The method of claim 1 wherein biomass is selected from the group consisting of bioenergy crops, agricultural residues, municipal solid waste, industrial solid waste, yard waste, wood and forestry waste.

14. The method of claim 1 wherein biomass is selected from the group consisting of switchgrass, waste paper, sludge from paper manufacture, corn grain, corn cobs, corn husks, corn stover, corn fiber, grasses, wheat, wheat straw, hay, barley, barley straw, rice straw, sugar cane bagasse, sorghum, soy, components obtained from milling of grains, trees, branches, roots, leaves, wood chips, sawdust, shrubs and bushes, vegetables, fruits, flowers and animal manure.

15. The method of claim 14 wherein biomass is selected from the group consisting of corn cobs, corn stover, corn fiber, corn husks, sugar cane bagasse, sawdust, switchgrass, wheat straw, hay, rice straw, and grasses.

16. The method of claim 15 wherein biomass is selected from the group consisting of corn cobs, corn stover, corn fiber, sawdust, and sugar cane bagasse.

17. The method of claim 1 wherein biomass is derived from multiple feedstocks.

18. The method of claim 1 wherein ammonia is selected from the group consisting of ammonia gas, ammonium hydroxide, urea, and combinations thereof.

19. The method of claim 1 wherein (b) is carried out at a temperature of from about 4° C. to about 200° C.

20. The method of claim 14 wherein (b) is carried out at a temperature of from about 75° C. to about 150° C.

21. The method of claim 15 wherein (b) is carried out at a temperature of from greater than 90° C. to about 150° C.

22. The method of claim 1 wherein (b) is carried out for a period of time of up to about 25 hours.

23. The method of claim 17 wherein (b) is carried out for a period of time of up to about 8 hours.

* * * * *